United States Patent [19]

Sato et al.

[11] Patent Number: 4,648,395
[45] Date of Patent: Mar. 10, 1987

[54] SYNCHRONIZED FEED TYPE OXYGEN CONCENTRATOR FOR USE IN AN OPEN BREATHING SYSTEM

[75] Inventors: Toru Sato, Tottori; Kozo Moriya, Shiga, both of Japan

[73] Assignee: Sanyo Densihkogyo Co. Ltd., Okayama, Japan

[21] Appl. No.: 640,086

[22] Filed: Aug. 13, 1984

Related U.S. Application Data

[63] Continuation-in-part of Ser. No. 511,194, Jul. 6, 1983, abandoned.

[30] Foreign Application Priority Data

Jul. 7, 1982 [JP] Japan .................... 57-118063

[51] Int. Cl.⁴ ............................ A61M 16/00
[52] U.S. Cl. ...................... 128/204.23; 128/207.18
[58] Field of Search ............. 128/204.21, 204.23, 128/204.24, 204.26, 202.22, 207.18

[56] References Cited

U.S. PATENT DOCUMENTS

| | | | |
|---|---|---|---|
| 3,316,902 | 5/1967 | Winchel et al. | 128/204.23 |
| 3,611,178 | 10/1971 | McConnell | 128/204.23 |
| 3,831,596 | 8/1974 | Cavallo | 128/204.23 |
| 4,050,458 | 9/1977 | Friend | 128/204.23 |
| 4,187,842 | 2/1980 | Schreiber | 128/202.22 |
| 4,316,182 | 2/1982 | Hodgson | 128/204.23 |
| 4,326,513 | 4/1982 | Schulz et al. | 128/204.23 |
| 4,331,455 | 5/1982 | Sato | 55/21 |
| 4,357,936 | 11/1982 | Ellestad et al. | 128/204.23 |
| 4,381,774 | 5/1983 | Schreiber et al. | 128/202.22 |
| 4,414,982 | 11/1983 | Durkan | 128/204.24 |
| 4,428,372 | 1/1984 | Beysel et al. | 128/205.24 |
| 4,567,888 | 2/1986 | Robert et al. | 128/207.18 |
| 4,584,996 | 4/1986 | Blum | 128/204.21 |

FOREIGN PATENT DOCUMENTS

59-77864 5/1985 Japan .

OTHER PUBLICATIONS

Sato et al., "Patient-Triggered Insufflation", M.A. News, vol. IV, No. 11, (Nov/1983).

Primary Examiner—Henry J. Recla
Attorney, Agent, or Firm—Cushman, Darby & Cushman

[57] ABSTRACT

An oxygen concentrator for supplying enriched oxygen gas to an open breathing system of a human being or the like in synchronization with a breathing cycle of a patient is disclosed, comprising a thermocouple sensor and a control device for synchronizing the timing of opening an electromagnetic valve provided in the gas passageway with the beginning of an inhalation phase of the breathing cycle. The thermocouple sensor, located near the patient's nostrils detects the change in temperature of breathing air flow of the human being or the like and generates a detection signal indicating the instantaneous temperature of the breathing air flow. Thereafter, the control devices detects the beginning of an inhalation phase by comparing the successive two voltage levels of the detection signal. When the breathing cycle enters the inhalation phase, the control device opens the electromagnetic valve thereby permitting the flow of oxygen to the patient. Supplying oxygen only on the inhalation phase has the effect of remarkably increasing the efficiency of the oxygen concentrator moreover the detection signal is monitored to detect when the breathing cycle of the patient becomes irregular. Upon detection, the control device will supply oxygen continuously while giving an alarm signal so that emergency measures can be taken.

11 Claims, 12 Drawing Figures

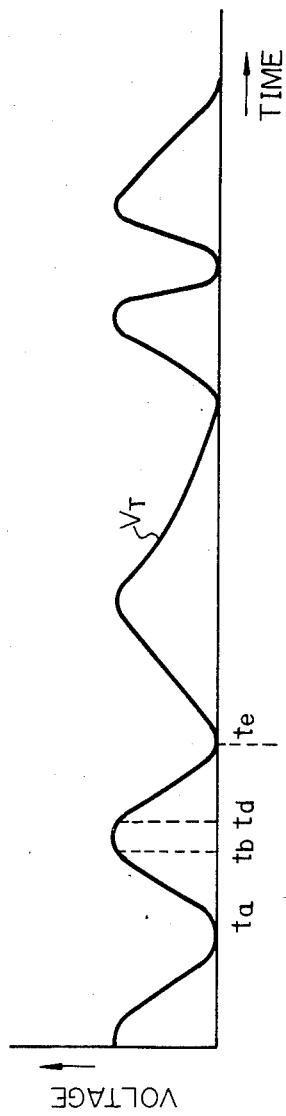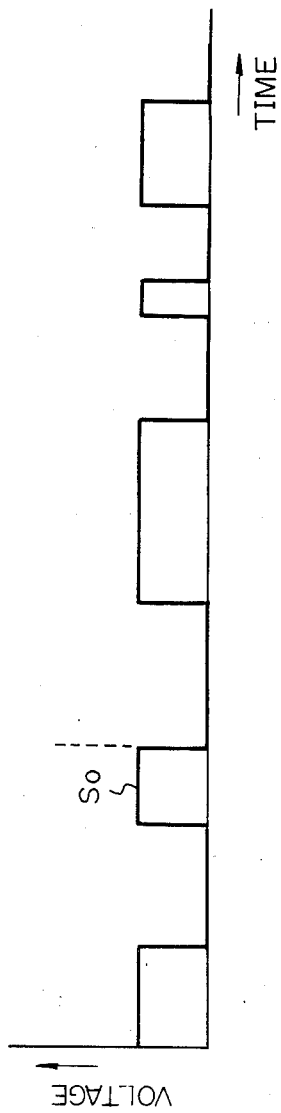

SYNCHRONIZED FEED TYPE OXYGEN CONCENTRATOR FOR USE IN AN OPEN BREATHING SYSTEM

BACKGROUND OF THE INVENTION

1. Field of the Invention

The present invention relates generally to an oxygen concentrator and more particularly to a synchronized feed type oxygen concentrator for supplying enriched oxygen gas to a breathing system of a human being, or the like, in an open breathing circuit in synchronization with a breathing motion of the human being, or the like, and is a continuation-in-part of our co-pending U.S. application Ser. No. 511,194 filed on July 6, 1983, now become abandoned and whose disclosure is incorporated by reference herein.

2. Prior Arts and Problems

With the recent progress in the medical arts, an increasing number of oxygen concentrators in inhalation therapy have been provided for patients suffering from respiratory ailments or circulatory diseases. It should be noted that oxygen concentrations for home use have become remarkably popular recently, as they are capable of concentrating the oxygen in the air by the use of an electric power source in the house through a simple operation, and supplying such concentrated oxygen gas for a medical use. Such an oxygen concentrator can eliminate the inconvenience of being dependent on an oxygen supply contained in cylinders, particularly in such countries where medical treatment at home prevails.

The methods of allowing the patients to inhale such gases as oxygen, etc. are generally classified into two categories, i.e. the so-called "closed circuit method" and the "open circuit method". The closed circuit method uses a facemask apparatus or an endotracheal tube inserted in the trache of the patient to provide the supply of gas such that the connection between the breathing circuit, comprising the respirator or gas supply system, and the breathing system of the patient is made airtight. This closed circuit method has an advantage in better inhalation effect while it causes such disadvantages as stimulation and discomfort, which are inflicted on the patient by covering the mouth and nose of the patient or by inserting a foreign substance directly into the trache. Therefore, this closed circuit method is mainly used for unconscious or seriously sick patients. On the other hand, the open circuit method allows the breathing circuit to be exposed to the open air. The tip of the gas supplying tube is inserted into the nostril or the mouth of the patent to feed the gas without requiring close contact for keeping an airtight connection between the apparatus and the face or upper airway, thereby reducing ill feeling or stimuli and allowing the patient to eat or drink, and speak even during inhalation treatment. Accordingly, this method is popularly used for mild cases where self-breathing is possible.

In the closed type breathing apparatus, oxygen may be supplied in response to the patient's actual breathing by detecting to change in pressure of the gas in the closed circuit. However, in a conventional open type breathing apparatus, a constant flow of gas is supplied independently of the breathing motion. As such, gas may be blown in during exhalation and the patient suffers from ill feeling, or most of the gas may be wasted by being exhaled back to open air without being used. Furthermore, since the open type breathing system is open to the environment, the concentration of the oxygen gas to be inhaled may be reduced. It has been a normal practice to increase the flow rate of the gas to cope with the reduction in concentration.

Oxygen concentrators are classified into two types, i.e., the so-called membrane type and the molecule adsorption type. The membrane type oxygen concentrator is adapted to direct the air through a membrane where oxygen molecules and nitrogen molecules are separated in order to increase the concentration of oxygen. In this method the maximum attainable concentration of oxygen will be at most 40%. For this reason, this method is more suitable for closed breathing systems using a facemask or the like. In the molecule adsorption type (also to be referred as "pressure swing adsorption" type), air is directed through an adsorption tube filled with a particular substance (adsorption agent) and by changing the pressure of the air flow, the nitrogen and water contained in the air are caused to be more highly adsorbed and desorbed compared to the oxygen in the air so as to be separated from each other to attain finally highly concentrated oxygen. By this method, oxygen concentration higher than 90% can be obtained. Therefore, this method is suitable for long inhalation by use of an open type breathing system. However, as the concentrated gas is used more and more, the quantity of the purging gas usable for regeneration of the adsorption agent will be reduced. In this respect, the inherent purpose of the oxygen concentrator may be inhibited. As the countermeasure for solving this problem, efforts have been made to enlarge the oxygen concentrator itself or improve the technical performance but there have been certain limits for such efforts.

In our parent patent application mentioned above, there is disclosed an oxygen gas supply system for effectively feeding gas to a breathing system of a human being, or the like, in an open breathing circuit in synchronization with the breathing motion. The gas supply system comprises an apparatus for controlling the supply of gas in synchronization with the breathing motion of the human being or the like. The apparatus for controlling the supply of gas includes a thermocouple sensor for detecting the temperature of the breathing air flow and for generating a detection signal representative of the instantaneous temperature. Such a detection signal is amplified to a desired level and preferably transmitted through a low pass filter for noise removal. The obtained detection signal is supplied to holding means and comparator means. The holding means and the comparator means operate to generate an enabling pulse just before a breathing cycle enters an inhalation phase (hereafter sometimes referred to as a breath-in phase). The enabling pulse operates on a one-shot circuit to permit supply of oxygen for a predetermined period of time in each breath-in phase of respiration.

Further, the holding means and the comparator means operate to generate an enabling pulse just before a breathing cycle enters a breath-in phase, and generate a disabling pulse just before the breathing cycle enters an exhalation phase (hereafter sometimes referred to as a breath-out phase). The enabling pulse switches a bistable means to a first state for commencing to supply gas and the disabling pulse switches the bistable means to a second state for halting the supply of gas, thus permitting the supply of gas for the whole duration of each breath-in phase.

Moreover, in the gas supply system described above, monitor means is provided to detect when the cycling period of the detection signal is beyond a pre-established safety limit and to change the supply of gas into a consecutive supply mode for an emergency measure while activating an alarm device.

The instant invention comprises an improvement over the invention disclosed in the parent patent application by providing an oxygen gas reserving apparatus which ensures that the oxygen gas can be supplied at a high rate to the breathing system of the patient even though the amount of the enriched oxygen gas to be produced per unit time remains unchanged. Furthermore, the instant invention comprises a timer device for establishing a time for closing a valve provided in the oxygen passageway of the system whereby arterial oxygen pressure ($P_a O_2$) of a human being or the like can be effectively increased.

OBJECTS OF THE INVENTION

Accordingly, it is an object of the present invention to provide an improved oxygen concentrator having much higher performance and efficiency in producing concentrated oxygen gas from the ambient air and in the in feeding concentrated oxygen gas to a patient in an open breathing circuit than those of the conventional molecule adsorption type oxygen concentrator which is adapted to use an adsorption agent and is capable of selectively adsorbing the gas and providing gas in response to a pressure change. It is another object of the present invention to provide a novel oxygen concentrator which is compact in size and light in weight and also saves energy.

SUMMARY OF THE INVENTION

In the prior art oxygen concentrator, concentrated oxygen gas is continuously supplied regardless of the breathing pattern of a human being or the like. Therefore, during exhalation, the concentrated oxygen gas is exhaled into the open air only to be wasted. According to the present invention, a synchronization device is provided in the oxygen concentrator. The temperature change during exhalation and inhalation may be sensed together with the time of breathing by a thermocouple sensor provided in front of the nose of a patient. The temperature change is converted into a thermo-electromotive force which will be electrically amplified and controlled by a control unit to cause an electromagnetic valve, adapted to synchronize with the beginning of inhalation, to be opened so that concentrated oxygen gas may be fed during the time of inhalation. Since the concentrated oxygen gas will not be used even though it is fed during the time of exhalation, the synchronizable electromagnetic valve will be kept closed during the time of exhalation and supply of the gas is suspended. The amount of the concentrated gas which will be kept in a reservoir or inside the piping due to suspension of the gas supply, as discussed above, may be added to the oxygen gas to be fed at the time of inhalation. Therefore, although the amount of the concentrated gas to be generated per unit time remains unchanged, the oxygen gas may be supplied at a higher rate, intermittently only at the required time and the percentage of the concentrated oxygen gas contained in the breathing air flow of the human being, or the like may be increased.

Furthermore, the part of the breathing air near the end of the breathing pattern of a human being or the like, will not reach the respiratory organs but fill only the dead space. Since that part of the gas is not used by the respiratory organs, it may be blown out by opening the synchronizable electromagnetic valve at the beginning of the next inhalation. By properly establishing the time of closing the synchronizable electromagnetic valve with a timer device, it is possible to effectively increase the arterial oxygen pressure ($P_a O_2$) of a human being or the like. Consequently, since the amount of the concentrated oxygen gas, of which supply has been suspended from the oxygen concentrator, may be utilized as the purging gas for regenerating the adsorption agent in the oxygen concentrator, the oxygen concentrator according to the present invention, as compared with the equivalent conventional concentrator, may improve the performance by roughly more than 200% (refer to FIG. 10) and the improvement of the performance may correspondingly be contributed to reduction in size and weight, and energy saving in the oxygen concentrator. In this way, it is possible to provide an oxygen concentrator which is capable of remarkably improving performance, as compared to the conventional one.

Furthermore, a safety device is also provided which can generate an alarm and at the same time keep the valve open to continuously feed the concentrated oxygen gas when the breathing sensing signals are not input during a given period of time.

BRIEF DESCRIPTION OF THE DRAWINGS

These and other objects and many of the attendant advantages of the present invention will be readily appreciated as the same becomes better understood by reference to the following detailed description when considered in connection with the accompanying drawings, in which:

FIG. 6 is a waveform diagram of a detection signal obtained by a thermocouple sensor in accordance with the present invention, wherein the period of the breathing cycle varies with time;

FIG. 7 is a timing chart of an activation signal obtained by the control circuit of FIG. 5;

DESCRIPTION OF THE PREFERRED EMBODIMENTS

Figure 1:
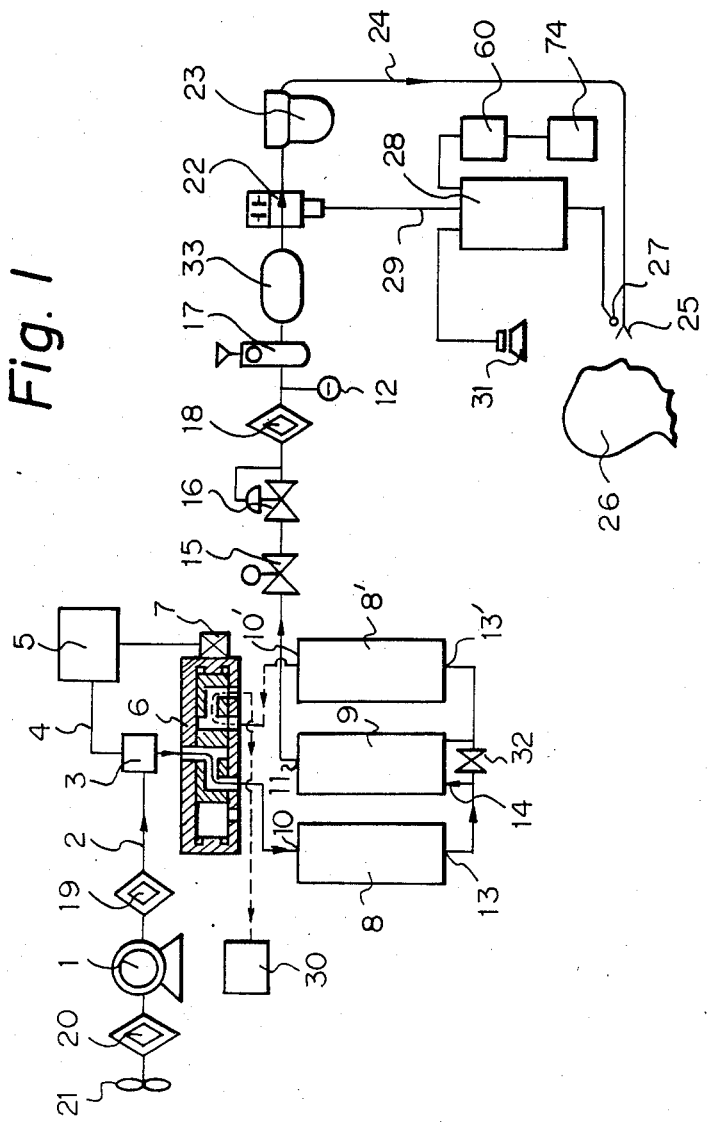
FIG. 1 is a schematic diagram showing a synchronized feed type oxygen concentrator embodying the present invention.

Referring to FIG. 1, adsorption tubes 8 and 8' containing dehumidifying and nitrogen-adsorbing agents are juxtaposed and a compressor 1 adapted to supply air to the tubes is provided. A fan 21 is attached to the compressor 1 and fresh air is supplied from the form to compressor 1 after removal of dust by a filter 20. The compressor land the fan 21 are energized when the electric power source is turned on. The compressed air supplied from the compressor 1 is further purified by the dedusting filter 19 and supplied through a conduit 2 to a port of a 5-way electromagnetic valve 6 which supplies the compressed air alternately to the adsorption tubes 8 and 8'. When the pressure of the compressed air which has been supplied to said inlet of the valve 6 exceeds a predetermined value, a pressure switch 3 will cause the electrical contact to be switched on. A conduit to the gas port 10 of the adsorption tube 8 is connected to one of the remaining four ports of the 5-way electromagnetic valve 6 and a conduit to the gas port 10' of the adsorption tube 8' is connected to another one of the remaining ports of said valve. The remaining two ports provided at the ends of the adsorption tubes serve as the exhaust ports which are designed to collect the desorbed gas in the adsorption tubes. A pressure reduction silencer 30 is connected before the exhaust ports, thus exhausting the desorbed gas to the outside. The air is introduced into the adsorption tube 8 from the gas port 10, where the nitrogen will be adsorbed by the nitrogen adsorbing agent and the concentrated oxygen will be extracted by way of the outlet 13. The outlet 13 for the concentrated oxygen of the adsorption tube 8 is connected to the outlet 13' for the concentrated oxygen of the other adsorption tube 8' by a conduit connected to a buffer tank 9 for storing the concentrated oxygen and a throttle valve 32. The concentrated oxygen may be stored in the buffer tank 9, while a part of the stored oxygen may be blown into adsorption tube 8' from the outlet 13' via a throttle valve 32 for washing out the water and nitrogen gas absorbed in the previous cycle by the adsorbing agent in the adsorption tube 8', thereby serving to recover the adsorption capability of the adsorbing agent by way of diffusion and desorption. The gas port 10' of the adsorption tube 8' is connected to the 5-way electromagnetic valve 6 and the gas to be exhausted out of the gas port 10' will be reduced in pressure and noise by the pressure reduction silencer 30 and then expelled to the atmosphere. As the compressed air is supplied to the adsorption tube 8 and adsorption of the nitrogen proceeds, the internal pressure in the adsorption tube 8 may be increased, thus causing the pressure required for sending the gas to be increased. When the above pressure exceeds the predetermined value, the pressure switch 3 will be activated and the appropriate signals will be communicated to the control unit 5 via a line 4. The control unit 5 will cause a switching signal to be fed to the coil of the electromagnetic valve to energize a slide unit adapted to switch the gas passages in the 5-way electromagnetic valve, whereby the compressed air previously being sent to the gas port 10 of the adsorption tube may be switched to the gas port 10' of the adsorption tube. The adsorption tube 8', in which adsorption capability has been recovered, can serve to concentrate (or enrich) the oxygen and supply it to the buffer tank 9 through the port 13' as well as to the other adsorption tube 8 through the orifice 32 so as to purge tube 8 with enriched oxygen gas and recover the adsorption capability of the tube 8. With such cycles being repeated, the concentrated oxygen may be stored in the buffer tank 9.

A shut-out valve 15 is provided at the outlet of the buffer tank 9 so that the oxygen gas may be prevented from flowing out of the tank. However, said valve is normally open while the oxygen concentrator, according to the present invention, is being operated. Since a pressure reducing valve 16 is connected to the tank, the oxygen gas may be supplied at a properly reduced pressure. Then the oxygen gas will be filtered through a bacteria filter 18 so as to provide a patient with a supply of filtered concentrated oxygen gas. After the bacteria filter 18 an oxygen concentration meter 12 is connected so that an operator such as a doctor, nurse or other occupational personnel as well as a patient may observe the concentration of the oxygen. To the concentrated oxygen supply conduit is connected nasal cannulae 25 by a flexible pipe 24 through the flow meter 17, gas storage tank 33, humidifier 23, and the electromagnetic valve 22 which is synchronizable with the breathing of the patient. A patient can inhale the concentrated oxygen through the nasal cannulae.

The flow meter 17 is equipped with a mechanism for adjusting the flow control valve to supply a suitable flow rate of the concentrated oxygen for the patient 26 in question.

Figure 11:
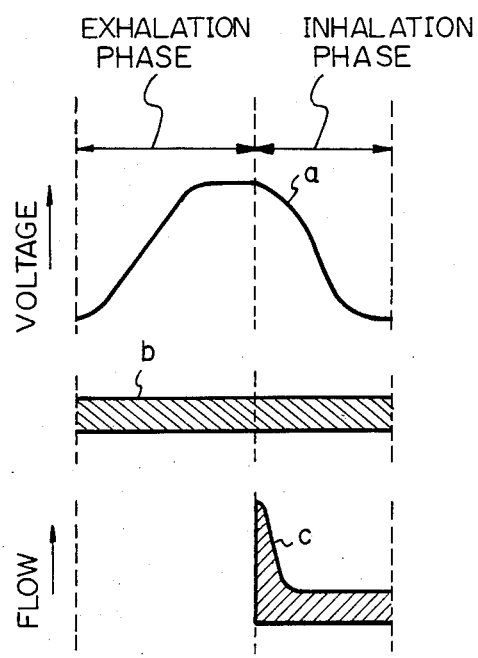
FIG. 11 is a schematic diagram for illustrating the relations among a voltage level (a) off a detection signal obtained by a thermocouple sensor, an outflow (b) of the conventional oxygen concentrator which continuously supplies oxygen gas at a given constant rate, and a peaked outflow (c) of the synchronized feed type concentrator feeding oxygen gas in synchronization with the breathing motion.

The gas storage tank 33 is so designed that when the electromagnetic valve 22 is opened, the tank may supply a peak flow rate in a pulse form at the initial stage of the valve being opened as shown in FIG. 11(c). If the concentrated oxygen gas will be supplied in a waveform as described above, it may be efficiently used by the patient 26 for inhalation.

The electromagnetic valve 22 is adapted to receive the an on-off signal, in synchronization with the breathing of the patent, from the control unit 28 through the communication cable 29, and open or close the valve 22 correspondingly whereby the concentrated oxygen gas stored in the gas storage tank 33 may be supplied intermittently in synchronization with the actual breathing. The control unit 28, which controls the supply of the gas through the nasal cannulae 25, is adapted to detect, by way of a thermocouple type temperature sensor 27, the change in air temperature at the time of exhalation and inhalation by a patient, feed the detected results back to the control unit 28 and provide the control signals for operating the electromagnetic valve 22. A detailed explanation of the process will follow. The humidifier 23 serves to humidify the concentrated oxygen gas to the extent suitable for inhalation by a patient.

Figure 2:
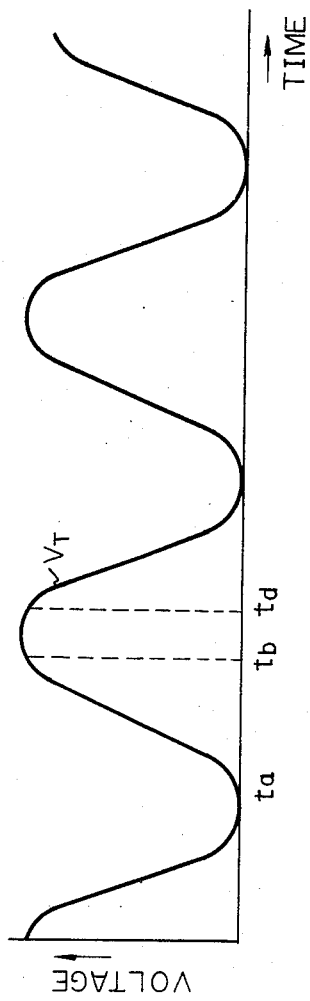
FIG. 2 is a waveform diagram of a detection signal obtained by a thermocouple sensor in accordance with the present invention.
Figure 3:
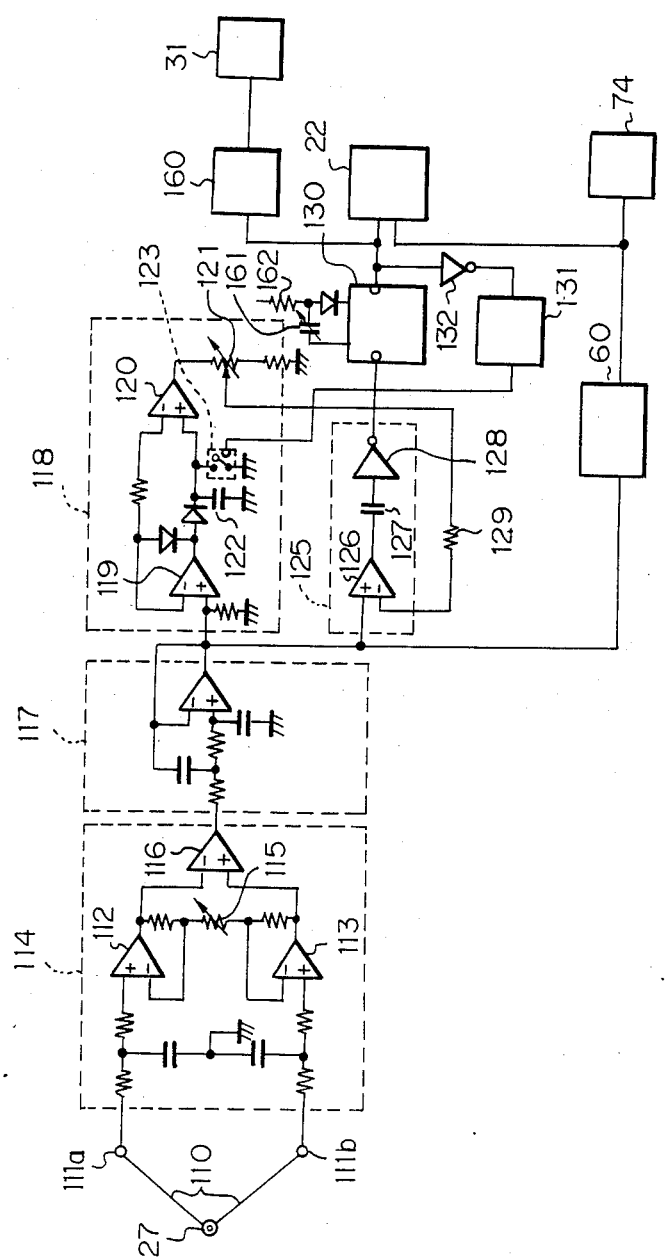
FIG. 3 is a circuit diagram showing an example the control apparatus according to the present invention.

The temperature sensor 27 provided at the nozzle portion of the nasal cannulae 25 should be designed to be compact and light so that when placed in front of the nose of a patient 26, the patient may easily hold it, and may not feel breathing resistance or feel uncomfortable. Furthermore, the sensor 27 should be highly responsive to the change in air temperature. The temperature sensor 27 is a type of thermocouple according to the present invention. As shown in FIG. 3, the output of the sensor 27 is connected to the input terminals 111a, 111b of the control unit 28 via a lead wire 110. The temperature sensor 27 is exposed to the air flow breathed through the nostril, senses the temperatures of the breathed air flow and generates a voltages corresponding to the sensed temperatures. Namely, the output voltage VT generated by the sensor 27 is gradually increased in the exhalation phase wherein breathing air is exhaled and gradually decreased in the inhalation phase when open air and the supplied concentrated oxygen gas are inhaled from outside. This results in a time wave substantially similar to a sine wave as shown in FIG. 2.

Referring to FIG. 3, the control unit 28 includes a pair of input terminals 111a, 111b which receive the detection signal $V_T$ from the sensor 27 through a pair of lead wires 110. The input terminals 111a, 111b are connected to non-inverting inputs of operational amplifiers 112, 113 which constitute a differential amplifier 114. A variable resistor 115, both terminals of which are connected to inverting inputs of the operational amplifiers 112, 113 respectively, serves to control the gain of the amplifier 114. The outputs of the operational amplifiers 112, 113 are connected to both inputs of an operational amplifier 116 of the output stage. The output of the operational amplifier 116 is connected through a low-pass filter 117, for reduction of noise, to a non-inverting input of an operational amplifier 119 of a holding circuit 118 and to a non-inverting input of an operational amplifier 126 of a comparator or enabling pulse generator 125.

The holding circuit 118 operates during each exhalation phase and during the transition to the immediately succeeding inhalation phase to cause a capacitor 122 to charge as the detection signal or input voltage gradually increases thereby holding the voltage level of the detection signal. The output voltage from the holding circuit 118 is connected to an inverting input of the operational amplifier 126 through a variable resistor 121 and a resistor 129. The resistor 121 serves to adjust such output voltage or voltage level, held by the circuit 118, for controlling the timing at which an enabling pulse is generated, as described hereinafter.

The operational amplifier 126 operates as a comparator which compares the current voltage level of the detection signal $V_T$ at the non-inverting input with the voltage level held by the circuit 118 at the inverting input to provide a comparison output. Namely, the operational amplifier 126 generates a high output voltage as the comparison output when the current voltage level at the noninverting input is higher than the voltage level at the inverting input. In contrast with this, when the voltage level at the noninverting input is lower than the voltage level at the inverting input, the amplifier 126 produces a low output voltage. The output of the comparator 126 is connected through a capacitor 127 and an inverter 128 to an input of a one-shot circuit 130 which is a kind of timer circuit for generating an output pulse having a predetermined duration at the leading edge of an input pulse. The one-shot circuit 130 may comprise a monostable multivibrator which is triggered at the leading edge of an input pulse to generate a pulse having a predetermined duration. This predetermined duration can be optionally established by adjusting apparatuses such as a variable condensor 161 and a resistor 162 of this embodiment which determine a time constant of the one-shot circuit 130. The output of the one-shot circuit 130 is connected to the electromagnetic valve 22 which is energized by the output pulse from the one-shot 130 to efficiently supply oxygen gas of high concentration, which gas is reserved within the tank 33, to the patient.

The output of the one-shot circuit 130 is also connected to the input of a hold-reset circuit 131 through an inverter 132. The switch 123 is normally open. The hold-reset circuit 131 may be a monostable multivibrator that is triggered at the leading edge of an input pulse to provide a pulse of a predetermined duration so as to close the switch 123. When the switch 123 is closed, the capacitor 122 discharges and the holding circuit 118 is reset.

In operation, the detection voltage signal $V_T$ being sent from the sensor 27 through the lead wire 110 is received by the pair of input terminals 111a, 111b and amplified in the amplifier 114 to a desired level. Thereafter, the signal $V_T$ is applied to the low-pass filter 117 which removes high frequency noises from the signal $V_T$. Then, the signal $V_T$ is applied to the holding circuit 118 and to the enabling pulse generator 125. When the patient 26 breathes out, the signal $V_T$ gradually increases with time, for example during $t_a$-$t_b$, and accordingly the current voltage level at the non-inverting input of the comparator or operational amplifier 126 is higher than the voltage level being held by the circuit 118 at the inverting input of the comparator 126. Thus the comparator 126 provides a high output voltage. When the breathing cycle enters a pause interval at $t_b$, the signal $V_T$ reaches its maximum or peak level and remains at the same voltage level. At that time, the current voltage level becomes equal to the voltage level being held by the circuit 118. However, the output of the comparator 126 can be maintained at a high voltage level by adjusting the variable resistor 121 to set the voltage level held by the holding circuit 118 to be slightly below the peak level by a predetermined amount.

Figure 4:
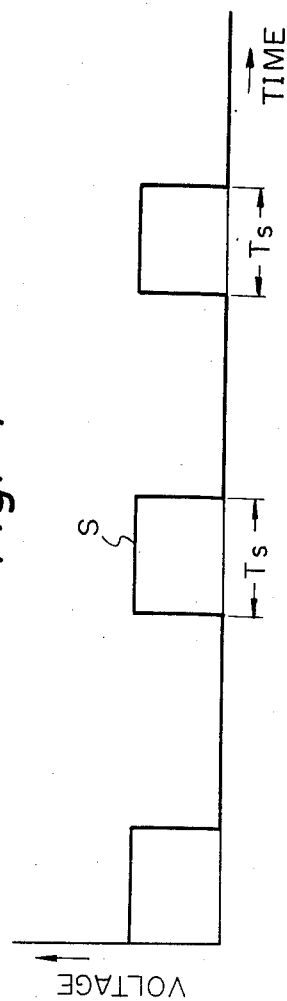
FIG. 4 is a timing chart of an activation signal obtained by the control circuit of FIG. 3.

When the breathing cycle enters an inhalation phase at $t_d$, the signal $V_T$ begins to decrease. Hence the current voltage level drops below the voltage level being held by the circuit 118. The output of the comparator 126 transitions to a low voltage level, causing the inverter 128 to generate a positive voltage pulse. The one-shot circuit 130 is triggered at the leading edge of the pulse to generate an activation pulse S with a fixed duration $T_S$ as shown in FIG. 4. The pulse S energizes the valve 22 to supply oxygen gas for the period of time $T_S$.

When the pulse S falls to a low voltage level i.e. the output voltage rises to a high voltage level, a positive voltage pulse is applied from the inverter 132 to the hold-reset circuit 131 which in turn is triggered at the leading edge of the pulse to generate an output pulse having a predetermined duration sufficient to discharge the capacitor 122. The output pulse from the circuit 131 enables the switch 123 to establish a circuit for discharging the capacitor 122, thus resetting the holding circuit 118. When the breathing cycle enters the next inhalation phase, the same operation will be performed repeatedly.

In accordance with the embodiment as shown in FIG. 3, a one-shot circuit is provided which responds to the enabling pulse to generate a forced pulse energizing the supply valve for a fixed period of time in each inhalation phase. In addition, a low-pass filter for removing noise from the detection signal is provided for the purpose of stable operation free from malfunctions. It is thereby assured that oxygen gas is supplied to the patient for a desired time only, that is, a predetermined time after the patient begins to breathe in.

Figure 5:
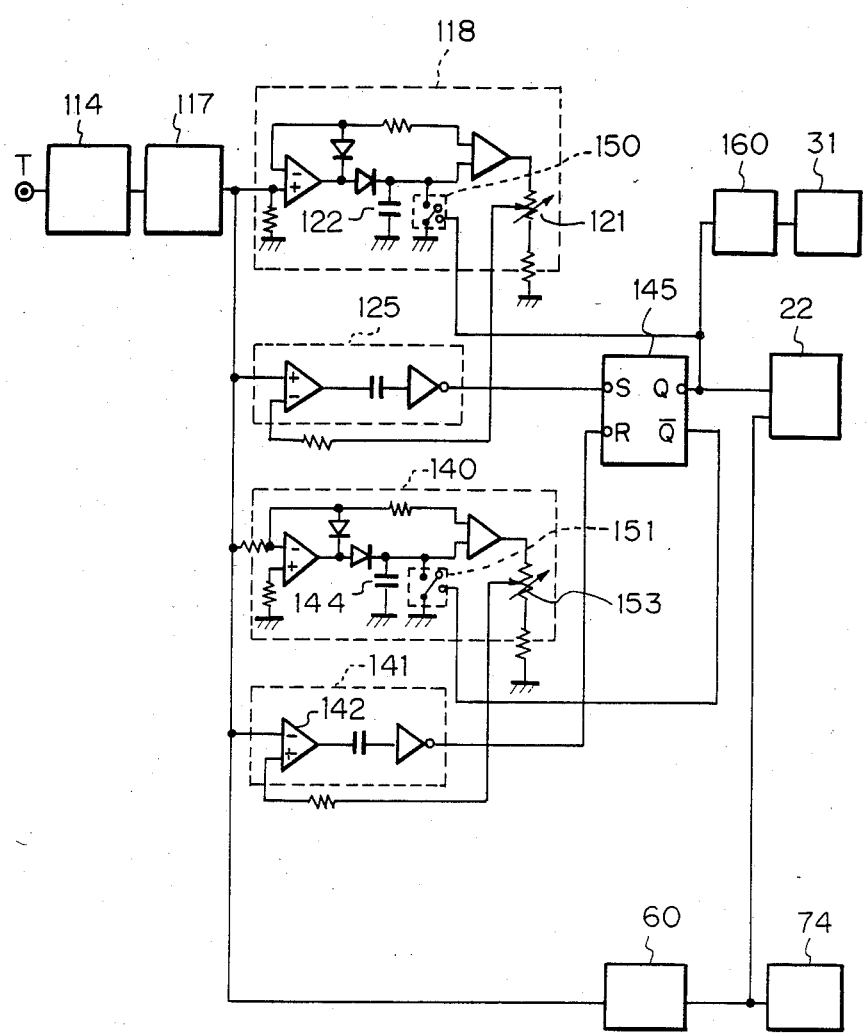
FIG. 5 is a circuit diagram showing another example of the control apparatus according to the present invention.

Referring to FIG. 5, a control unit in accordance with another embodiment of the present invention further comprises a second holding circuit 140 and a second comparator or disabling pulse generating circuit 141. In FIG. 5, like reference numerals designate corresponding parts shown in FIG. 3. The output of the low-pass filter 117 is connected to the inputs of the first holding circuit 118 and timing pulse generating circuit 125, and to the inputs of the second holding circuit 140 and comparator 141. The circuit 140 and comparator 141 may be the same elements or parts as the circuits 118 and 125 except that the input connections, particularly of operational amplifiers, are reversed. Thereby, the circuits 140 and 141 operate approximately 180 degrees out of phase with the first circuits 118 and 125. The output of the enabling pulse generator 125 is connected to a set terminal (S) of a flip-flop 145 while the output of the disabling pulse generator 141 is connected to a reset terminal (R) of the flip-flop 145. When the flip-flop 145 receives the enabling pulse at the terminal (S), the flip-flop 145 generates the output of a high voltage level at the terminal (Q). In contrast, when the flip-flop 145 receives the disabling pulse at the terminal (R), the output voltage level of the flip-flop 145 falls down to a low voltage level.

In operation, during an exhalation phase and during this period of transition to a breath-in phase ($t_a$–$t_d$), the first holding circuit 118 and the enabling pulse generator 125 operate to generate an enabling pulse in the same manner as previously described with reference to FIG. 3. The enabling pulse is applied to the set terminal (S) of the flip-flop 145 which in turn transitions to a high voltage level as an activation pulse $S_O$ (FIG. 7) energizing the valve 22.

On the other hand, the second holding circuit 140 and the disabling pulse generator 141 start operating. However, during an inhalation phase, the output of an operational amplifier 142 is at a high voltage level and the output of the flip-flop 145 remains at a high voltage level. Accordingly, the activation pulse $S_O$ remains at a high voltage level so as to keep the valve 22 open during the inhalation phase.

When the breathing cycle enters a pause interval at $t_e$, that is, the end of the inhalation phase, the output of the operational amplifier 142 transitions to a low voltage level. This is achieved by adjusting a variable register 153 such that the output voltage of the first holding circuit 140 or the voltage level held by the first holding circuit 140 is set to the maximum or peak level during the pause interval. Consequently, the disabling pulse generator 141 provides a positive voltage pulse which is applied as a disabling pulse to the rest terminal (R) of the flip-flop 145. Hence the output of the flip-flop 145 falls to a low voltage level (FIG. 7), deenergizing the valve 22.

The flip-flop 145 as shown in FIG. 5 is used to reset the first holding circuit 118 and the second holding circuit 140. The output of the flip-flop 145 at the output terminal (Q) is connected to the switch 150 of the first holding circuit. When the breathing cycle enters an inhalation phase, the switch 150 is closed so as to make the capacitor 122 discharge and accordingly, the first holding circuit 118 become reset. Similarly, the output of the flip-flop 145 at the terminal ($\overline{Q}$) is connected to a switch 151 of the second holding circuit 140. When an exhalation phase begins, the switch 151 is closed so as to make a capacitor 144 discharge and thus the holding circuit 140 is reset.

In accordance with the embodiment as shown in FIG. 5, a disabling pulse generating circuit and a flip-flop are provided to generate a disabling pulse, when each breath-in phase is completed, for de-energizing the supply valve which has been energized since the breath-in phase was entered. It is therefore assured that oxygen gas is supplied to the patient while he breathes in, independently of variations in the length of period of breath-in phase. It is noted that the timings at which the enabling pulse and the disabling pulse are generated can be controlled by adjusting the resisters 121 and 153, respectively. Further, warning tones are generated in synchronization with the operation of the electromagnetic valve 22 as will be described hereinbelow. Control signals for opening or shutting the valve 22 are connected to the timer circuit 160 which determines the duration of an output signal thereof. The output signal of the timer circuit 160 is connected to a sounding body 31 which generates the warning tone in synchronization with the beginning of an inhalation phase. The timer circuit 160 may be a one-shot circuit as shown in FIG. 3 and further may be arranged to change the duration of the warning tone, for instance, by adjusting the capacity of a variable capacitor 161. The warning tone allows the patient to know the apparatus is operating normally and feel safe. Thus this oxygen concentrator is available for rehabilitation of a chronic respiratory disease invalid. It is further apparent to those skilled in the art that this oxygen concentrator can be provided with devices (not shown) for stopping the generation of the warning tones and for turning the sound volume of the warning tones down or up.

Figure 8:
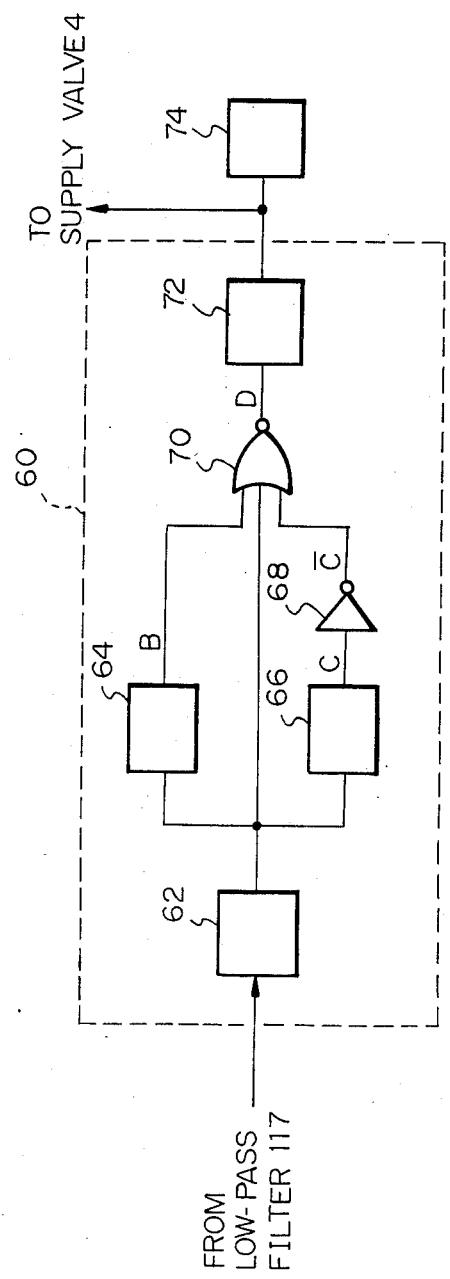
FIG. 8 is a circuit diagram of a monitor device in accordance with the present invention.
Figure 9:
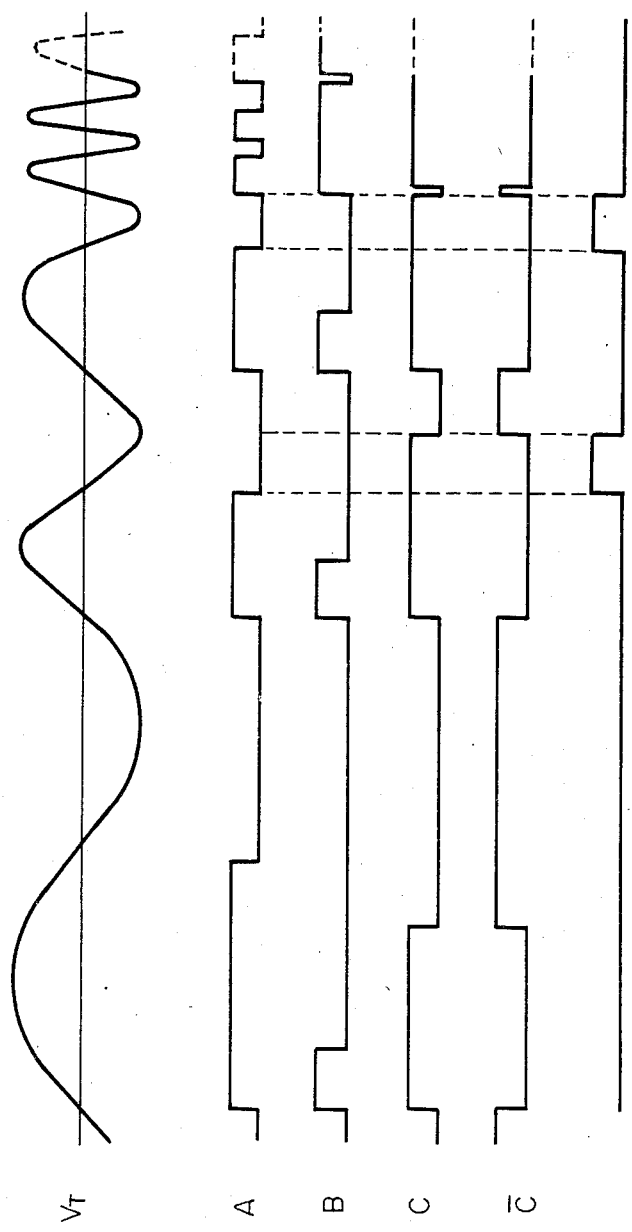
FIG. 9 is a timing chart for describing the operation of the monitor device of FIG. 8.

Referring next to FIG. 8, a monitor device in accordance with the present invention will be described. The monitor device is indicated at block 60 in FIGS. 3 and 5. In FIG. 8, the monitor device 60 comprises a waveform shaping circuit 62, two one-shot multivibrators 64, 66, an inverter 68, a NOR gate 70, and a timer circuit 72. The waveform shaping circuit 62 receives a detection signal $V_T$ having a substantially sinusoidal waveform from the lowpass filter 17 and shapes it into a squared voltage pulse A as shown in FIG. 9. The shaped signal A is applied to one input of the NOR gate 70 and to the inputs of the one-shots 64, 66. The one-shot circuit 64, which may be retriggerable, is triggered at the leading edge of the pulse signal A to generate an output pulse B having a preselected pulse length or duration, for example 2 sec. This pulse length provides a first or shorter safety limit. The output pulse B is applied to a second input of the NOR gate 70. On the other hand, the one-shot circuit 66 is triggered at the leading edge of the pulse signal A to generate an output pulse C having a preselected pulse length, for example 10 sec., which provides a second or longer safety limit. The output pulse C is applied to the inverter 68 and the inverted pulse $\overline{C}$ is applied to the remaining input of the NOR gate 70. The logic gate 70 provides a logical "0" output voltage if at least one of the pulses A, B and $\overline{C}$ is at a logical "1". However, if all the pulses A, B and $\overline{C}$ are at a logical "0", the gate 70 provides a logical "1" output voltage. It can be seen that such condition of "1" output is satisfied when the pulse length of A is longer than the pulse length (2 sec.) of B and shorter than the pulse length (10 sec.) of $\overline{C}$ or C, that is, when a half period of the breathing cycle is within 2 to 10 sec. The logical "1" output voltage from the gate 70 is applied as a reset pulse D to the timer circuit 72 for resetting the timer 72 in the middle of counting. The timer 72 may be set to 30 sec., for example. Thus, as long as the breathing cycle is normal, the timer 72 repeats its counting between the zero count and a middle or reset count without reaching the final or set count. The result is that no alarm signal appears at the output of the timer 72.

However, when the condition of the patient becomes worse and the breathing cycle is so irregular that a half breathing cycle or the length of the pulse A is shorter than the first safety limit of 2 sec. or longer than the second safety limit of 10 sec., the gate 70 no longer provides a logical "1" output voltage or reset pulse D. This permits the timer 72 to reach its set count and generate an alarm signal which is applied to the supply valve 4 and to an alarm device 74. This alarm signal makes the valve 4 open while activating the alarm device 74 which thus notifies the patient, nurse or other attendants of the emergency. It is noted that safety limits and the timer setting time may be changed depending on the individual, his disease etc.

Such a monitor device can be used not only with the control unit of FIG. 3 and FIG. 5, but with conventional closed-type supply systems. If the patient is affected by a fault in a closed-type system, such as damage to a tube or a disconnection of a joint portion, the monitor device operates to provide emergency measures and an alarm in the manner as described above. As described above, in the synchronized feed type oxygen concentrator according to the present invention, the timings of opening and of shutting the electromagnetic valve are synchronized with the beginning and the end of the inhalation phase in terms of the control unit as shown in FIG. 3 or FIG. 5, respectively so that the enriched oxygen gas can be supplied to the patient only during the inhalation phase. Such intermittent supply of oxygen gas results in a remarkable improvement in the technical efficiency of the oxygen concentrator.

Figure 10:
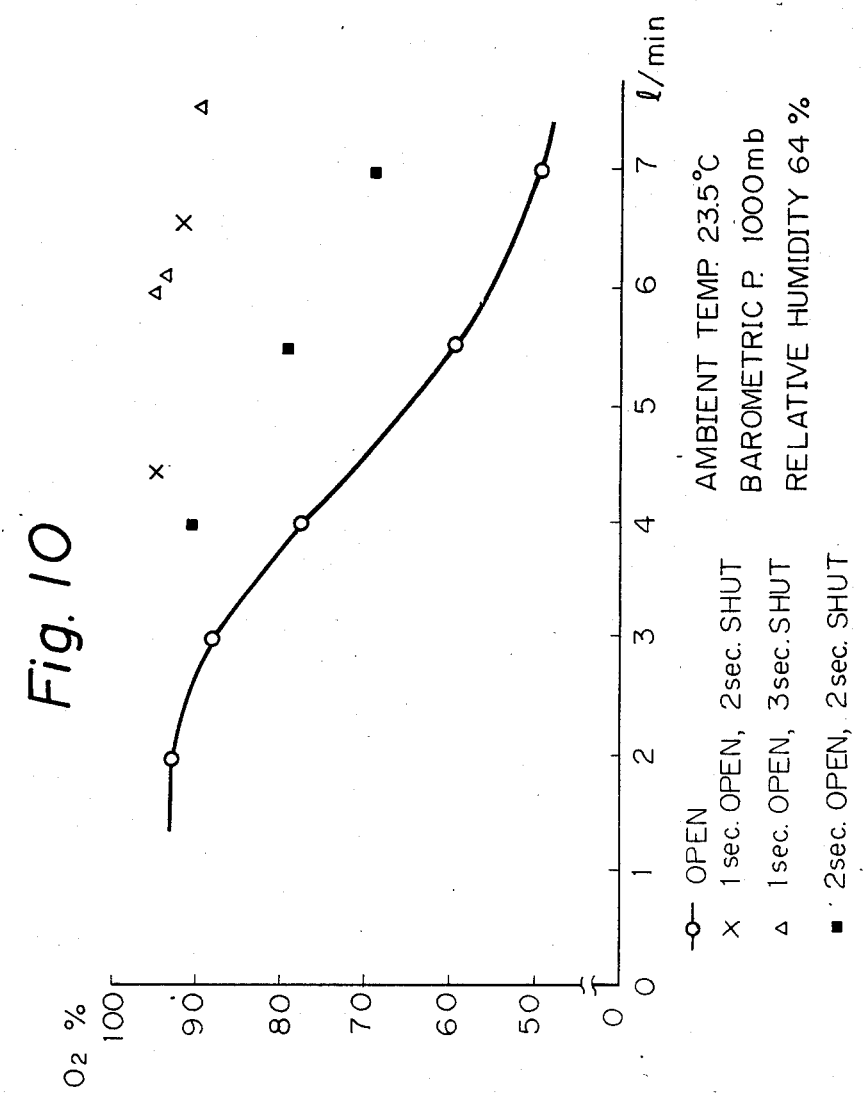
FIG. 10 is a graph illustrating outflowrates—$O_2\%$ characteristics of the synchronized feed type oxygen concentrator shown in FIG. 1.

The results of experiments on the effect of the oxygen concentrator according to the present invention are given in FIG. 10. In this figure, the curve including white circles indicates flowrates—$O_2\%$ characteristics of the prior art oxygen concentrator which feeds enriched oxygen gas to a patient continuously. As is seen from this graph, in the prior art, the percentage of oxygen gas ($O_2\%$) drastically reduces as the consumption of oxygen gas in the patient per minute increases gradually. In FIG. 10, black square dots indicate the $O_2\%$ in outflow of the oxygen concentrator measured under the condition that the electromagnetic valve opens for two seconds and closes for two seconds by turns. As shown in FIG. 10, the $O_2\%$ in outflow of the prior art oxygen concentrator is a mere 50% if the outflowrate is 7 liters per minute. In contrast, the $O_2\%$ in outflow of the oxygen concentrator intermittently supplying enriched oxygen gas under the above condition is about 70%. Since oxygen gas fed to the patient toward the end of the inhalation phase or in the pause interval stays in the trache of the patient and accordingly does not reach the inner parts of lungs of the patient, such oxygen gas is not available for the patient. Thus, the production of oxygen gas by the oxygen concentrator can be suppressed by regulating the timing of shutting of the electromagnetic valve while keeping the arterial oxygen pressure of the patient constant. In FIG. 10, crosses (X) indicate the $O_2\%$ in the outflow of an oxygen concentrator intermittently supplying the oxygen gas under the condition that the valve opens for one second and closes for 2 seconds repeatedly. Further, white triangles (Δ) indicate the $O_2\%$ in the outflow of an oxygen concentrator feeding the gas under the condition that the valve opens for one second and shuts for three seconds. In both cases, the $O_2\%$ reaches more than 90%. Accordingly, the synchronized feed type oxygen concentrator is very effective in miniaturizing the required components and in saving energies.

Hereinafter the special effects of the synchronized feed type oxygen concentrator supplying a peak-like flow of oxygen gas in synchronization with the respiration of the patient will be described.

Figure 12:
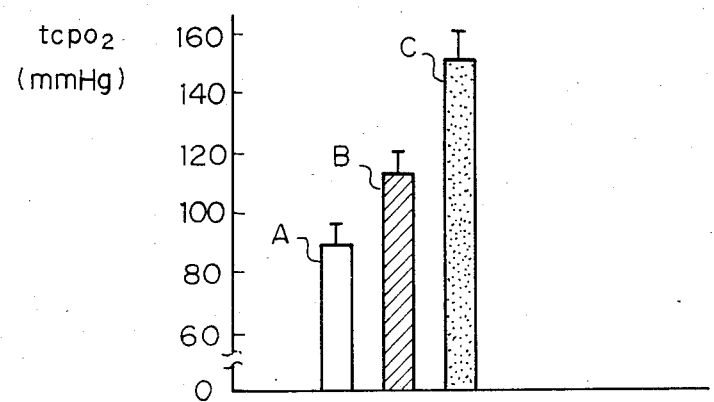
FIG. 12 is a graph for describing the special effects derived from the synchronized feed type concentration shown in FIG. 1.

FIG. 12 shows the results of experiments in which transcutaneous oxygen pressure (tcp $O_2$) is measured under the following conditions:
(A) A patient breathes open air without an oxygen concentrator.
(B) Constant flow of oxygen gas is fed to the patient.
(C) Peak-like flow of oxygen gas having the same rate of the flow as in the case (B) is supplied to the patient in synchronization with the beginning of the inhalation phase.

As shown in FIG. 12, the tcp $O_2$ obtained in the case (C) is greater than that obtained in the case (B) by 33% to 44%.

In order to supply the oxygen gas in such a manner as in the case (C), there must be a reduction in the synthetic impedance of the latter half of the gas supply system, that is, the part from the outlet port of the buffer tank 33 to the nasal cannula as much as possible. Therefore, the buffer tank 33 should be positioned as close as possible to the patient and preferably should be provided just in front of the inlet of the electromagnetic valve. Further, the construction of the humidifier 23 and the length of pipe 24 and so on should be arranged to decrease the synthetic impedance.

In addition, the capacity of the buffer tank 33 substantially influences the waveform of the gas flow. However, the tcp $O_2$ remains constant and independent of the capacity of the buffer tank 33 if the capacity of the tank is within the range from 100 milliliters to 400 milliliters.

The special effects and advantages derived from the present invention will be summarized hereinbelow.

(1) An oxygen concentrator intermittently supplying enriched oxygen gas to a patient in synchronization with the patient's respiration achieves a remarkable increase in technical performance by utilizing an amount of oxygen enriched gas, the supply of which has been suspended from the oxygen concentrator, as purging gas for regenerating the adsorption agent in the oxygen concentrator in comparison with the prior art continuous flow supplying concentrator.

(2) Therefore, such an oxygen concentrator supplying oxygen gas can reduce the size and weight required and effectively save the consumption of energy while retaining the same oxygenation ability as of the prior art concentrator.

(3) Since a buffer tank for reserving enriched oxygen gas is provided at the side of an inlet of the supply valve in an enriched oxygen gas flow passage, a stable flow of the enriched oxygen gas can be fed to a patient while the gas is being supplied in synchronization with the breathing motion of the patient.

(4) Appropriate adjustment of the timing of closing the electromagnetic valve, which is being opened at the beginning of an inhalation phase, can suppress the consumption of enriched oxygen gas to the minimum extent necessary for the patient while the arterial oxygen pressure of a human being is held constant.

(5) The synchronized feed type oxygen concentrator according to the present invention becomes available for the rehabilitation of a chronic respiratory invalid by generating warning tones in terms of electric signals synchronized with the patient's breathing.

The warning tones succeedingly let the patient know the fact that the oxygen concentrator is operating normally and lets him become comfortable, as well as letting him know the most suitable rythm of breathing for himself, thereby training himself according to his condition or operating conditions of this oxygen concentrator.

(6) The sensor for detecting the gas flow, which may be composed of only a copper-constantan thermocouple, and accordingly is so small and light thereby having the following advantages:

(i) The provision of the sensor into the nasal cannulae in front of the patient's nostril becomes much easier than the prior art and never disturbs the patient's breathing.

(ii) The mass production of the sensor becomes possible without causing any instability of performance of the sensor and becomes very usable because of its cheapness and disposability.

While the present invention has been particularly shown and described with reference to the preferred embodiment, it will be understood by those skilled in the art that various changes and modifications may be made therein without departing from the sprit and scope of the present invention.

What is claimed is:

1. In an open breathing circuit including a gas supply system and a breathing system of a human being or the like, said gas supply system supplying oxygen enriched gas produced from ambient air to said breathing system in synchronization with a breathing motion of said human being or the like through an open air type breathing system, comprising:

synchronized feed type oxygen concentration means for supplying oxygen enriched gas to said breathing system in synchronization with said breathing motion of said human being or the like, including:

thermocouple sensor means adapted to be positioned close to the nostrils of said human being or the like for generating an detection signal indicative of the instantaneous temperature of a breathing air flow of said human being or the like; and control means, coupled to said thermocouple sensor means, for detecting the beginning of an inhalation phase in a breathing cycle of said human being or the like by detecting substantially the beginning of a drop in temperature indicated by said detection signal, and for controlling said gas supply system so as to supply oxygen enriched gas to said breathing system only during said inhalation phase, said control means including:

amplifier circuit means, coupled to an output of said thermocouple sensor means, for amplifying a voltage level of said detection signal to a desired level;

holding means, coupled to an output of said amplifier circuit means, for holding a first voltage level of the amplified detection signal from said amplifier circuit means, said first voltage level being the voltage level of an output of said amplifier circuit means at a given moment;

comparator means, coupled to an output of said amplifier circuit means and to an output of said holding means, for comparing a second voltage level of said amplified detection signal with said first voltage level, said second voltage level being the voltage level of said amplifier circuit means at the moment when a predetermined period of time has passed since said first voltage level started to be held, and for generating an enabling pulse beginning the supply of gas when the absolute value of said second voltage level is less than the absolute value of said first voltage level, said first voltage level absolute value being arranged to be less than the absolute value of a predetermined portion of the maximum absolute value of said detection signal voltage level; and bistable means coupled to an output of said comparator means and being switched by said enabling pulse to a first state for commencing said supply of gas, and being switched to a second state for halting said supply of gas, thereby continuing to supply said gas for the duration of said inhalation phase.

2. The apparatus set forth in claim 1 wherein said control means includes an electromagnetic valve for controlling a supply of oxygen enriched gas to said breathing system.

3. The apparatus set forth in claim 2, further comprising a buffer reserving means attached to said electromagnetic valve for storing oxygen enriched gas and supplying said oxygen enriched gas to said electromagnetic valve in a stable fashion.

4. The apparatus set forth in claim 3 wherein said control means includes timer means for controlling the timing of the closing of said electromagnetic valve.

5. The apparatus set forth in claim 4 wherein said control means further includes:

monitor means, coupled to an output of said amplifier circuit means, for detecting when a frequency of change of said detection signal is outside a pre-established safety limit to generate an alarm signal and to put said supply of gas into a continuous supply mode.

6. The apparatus set forth in claim 5 wherein said monitor means includes:

signal shaping means, coupled to an output of said amplifier circuit means, for shaping said detection signal into a squared pulse;

first limit setting means, coupled to an output of said signal shaping means and triggered at the leading edge of said squared pulse, for generating a first pulse with a first preselected duration defining a first safety limit;

second limit setting means, coupled to an output of said signal shaping means and triggered at the leading edge of said squared pulse, for generating a second pulse with a second preselected duration defining a second safety limit;

logic means, coupled to an output of said signal shaping means and to outputs of said first and said second limit setting means, for logically combining said squared pulse, said first pulse and said second pulse to provide a logical "1" output when the duration of said squared pulse is shorter than said first safety limit or longer than said second safety limit; and timer means coupled, to an output of said logic means and being responsive to said logical "1" output, for generating said alarm signal after a preselected time delay.

7. The apparatus as set forth in claim 1, 2, 3 or 4 wherein said control means includes, in combination:
one-shot circuit means, coupled to the output of said comparator means and responsive to said enabling pulse, for permitting said gas to be supplied for a predetermined period of time in said inhalation phase.

8. The apparatus set forth in claim 7 further comprising timer circuit means, coupled to an output of said one-shot circuit and being responsive to said enabling pulse, for generating a pulse signal with a predetermined time delay, and switch means coupled to said holding means and being switched by said pulse signal for discharging the voltage of said first voltage level.

9. The apparatus set forth in claim 7, further comprising adjusting means, coupled to an output of said holding means, for adjusting said first voltage level.

10. The apparatus set forth in claim 1 wherein said holding means includes:
a first holding circuit coupled to an output of said amplifier circuit and being operative during a first breathing cycle to hold said first voltage level; and
a second holding circuit coupled to an output of said amplifier circuit and being operative during a second breathing cycle to hold said first voltage level; wherein said comparator means includes:
a first comparator circuit, coupled to an output of said amplifier circuit and to an output of said first holding circuit, for comparing said second voltage level with said first voltage level at the moment when a predetermined period of time has passed since said first voltage level started to be held, and for generating an enabling pulse for beginning the supply of gas when the absolute value of said second voltage level is less than the absolute value of said first voltage level, said first voltage level being less than the value of said predetermined proportion; and
a second amplifier circuit, coupled to an output of said amplifier circuit and to an output of said second holding circuit, for comparing said second voltage level with said first voltage level at the moment when said predetermined period of time has passed since said first voltage level started to be held, and for generating a disabling pulse for halting the supply of gas when the absolute value of said first voltage level is less than the absolute value of said second voltage level.

11. In an open breathing circuit including a gas supply system and a breathing system of a human being or the like, a method for controlling the supply of gas to said breathing system, comprising the steps of:
(a) detecting the temperature of a breathing air flow of said human being or the like and producing a detection signal, having a voltage level, representative of the instantaneous temperature of said breathing air flow, said voltage level being amplified by an amplifier to a desired voltage level;
(b) holding, during a predetermined period of time, a first voltage level of the amplified detection signal, said first voltage level being the voltage level of an output of said amplifier at a given moment;
(c) comparing a second voltage level of said detection signal with said first voltage level, said second voltage level being the voltage level of said detection signal at the moment when a predetermined period of time has past since said first voltage level started to be held in step (b), and producing an enabling pulse which permits gas to be supplied for a period of inhalation when the absolute value of said second voltage level is less than the absolute value of said first voltage level, said first voltage level absolute value being arranged to be less than the absolute value of a predetermined proportion of the maximum absolute value of said detection signal voltage level; and
(d) supplying gas in accordance with first and second supply states, said first state being enabled by said enabling pulse and supplying gas during inhalation, said second state halting said supply of gas.

* * * * *